(12) United States Patent
Regan et al.

(10) Patent No.: US 8,412,303 B2
(45) Date of Patent: Apr. 2, 2013

(54) ELECTRODE FOR USE WITH A TEMPLATE CAP

(75) Inventors: Shawn Regan, Columbia, SC (US); Isiah Daniel Smith, Lexington, SC (US); Katherine Hicks, Charleston, SC (US)

(73) Assignee: Rhythmlink International, LLC, Columbia, SC (US)

( * ) Notice: Subject to any disclaimer, the term of this patent is extended or adjusted under 35 U.S.C. 154(b) by 320 days.

(21) Appl. No.: 12/915,808

(22) Filed: Oct. 29, 2010

(65) Prior Publication Data
US 2011/0105878 A1    May 5, 2011

Related U.S. Application Data

(60) Provisional application No. 61/256,378, filed on Oct. 30, 2009.

(51) Int. Cl.
*A61B 5/0478* (2006.01)

(52) U.S. Cl. .......................... 600/383; 600/373

(58) Field of Classification Search .................. 600/383, 600/544
See application file for complete search history.

(56) References Cited

U.S. PATENT DOCUMENTS

| 5,928,143 A | 7/1999 | NcNaughton |
| 6,201,982 B1 | 3/2001 | Menkes et al. |
| 6,510,340 B1 | 1/2003 | Jordan |
| 2008/0154112 A1 | 6/2008 | Murphy et al. |

*Primary Examiner* — Lee S Cohen
(74) *Attorney, Agent, or Firm* — Michael A. Mann; Nexsen Pruet, LLC

(57) ABSTRACT

An electrode attached to the straps of and use with a template cap in making neurophysiological measurements. The electrode is configured to allow the user to quickly and accurately slide an electrode needle at a shallow adjustable angle into the scalp of the patient. The base of each electrode attaches to the cap at locations where measurements are to be made. The base supports a ramp that may be snapped into a clip on the base for storage and then springs resiliently from the clip when released. The electrode needle is carried by a slidable holder secured to the ramp at its slot and is slid forward following that slot when driving the needle down and through a small hole in the base of the electrode to insert it into the patient's scalp at the appropriate depth and angle.

20 Claims, 2 Drawing Sheets

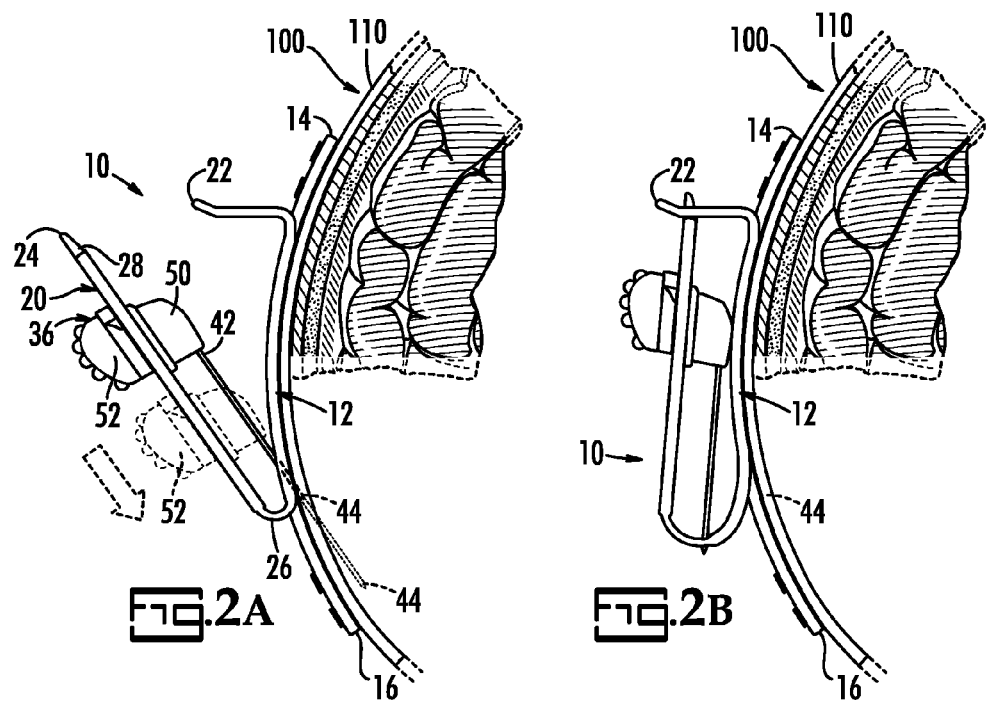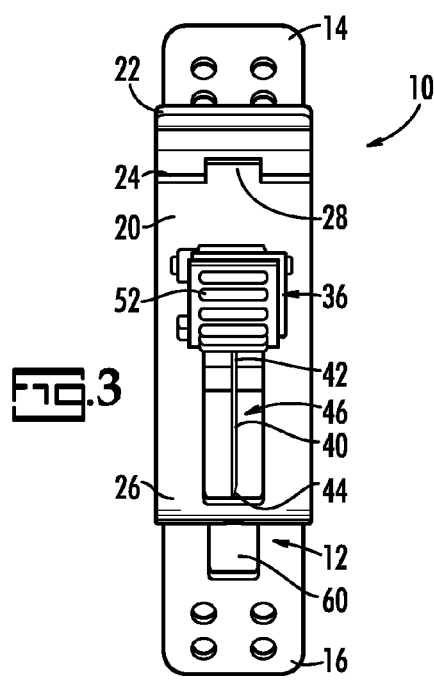

ELECTRODE FOR USE WITH A TEMPLATE CAP

PRIORITY CLAIM

Priority is claimed to U.S. Provisional patent application Ser. No. 61/256,378, filed Oct. 30, 2009, which is incorporated herein in its entirety by reference.

BACKGROUND OF THE INVENTION

Neurophysiological measurements such as electroencephalography or evoked potentials of a patient's brain can be made with electrodes attached to or placed within or under the scalp of the patient. Electrical signals can be generated by the brain and transmitted via the electrodes and the received responses recorded with neurophysiologic monitoring equipment. Electrodes vary from non-invasive cup electrodes which rest onto of the scalp to more invasive options such as needle electrodes which are inserted under the scalp.

Often multiple measurements are made on a patient at the same time and it has been found useful to have the measurements made using a standard set of locations on patients' heads so that the results of those measurements whether made sequentially on the same patient or on different patients, are more comparable. The International 10-20 System of Electrode Placement is an internationally recognized method used to describe the location of scalp electrodes.

To assist in placement of electrodes in these standard locations, template caps have been developed that fit the head of the patient and define the locations for the insertion or placement of the electrodes. See for example, U.S. Pat. No. 5,293,867, which is hereby incorporated in its entirely by reference.

However, having the locations defined does not completely address the need for being able to obtain the measurement data rapidly. Following an accident, for example, the sooner this data can be obtained, the better to determine the extent of the patient's injuries. The template cap tells where the electrodes are to be inserted or placed on the scalp of a particular patient but getting the electrodes inserted and receiving the measurement information still takes time and skill. Accordingly, there remains a need for a safe and simple way to start the process of recording brain activity as soon as possible, particularly after a head injury.

SUMMARY OF THE INVENTION

The present invention is an electrode for use with a template cap. The template cap can have the electrodes attached in advance at the standard locations where measurements are to be made and then the electrode needles are rapidly deployable into the scalp of the patient, even by those with limited training in neurophysiological measurements. The electrode holds a needle in a stored position and can quickly release it from the stored position to an insertion-ready position. The electrode has a base that supports a ramp that in turn carries a sliding holder in a slot formed in the ramp; the holder holds the electrode needle parallel to the ramp and poised over a small slot in the base. To insert the electrode needle, the user slides the holder down the ramp, through the slot in the base and into the scalp of the patient at the pre-designated location. The electrode and the holder are then in the inserted position.

An advantage of the present invention is that the electrode needles can be inserted quickly by those with little training. The template cap is placed on the head of the patient, the ramps of each electrode are released from their stored positions close to their bases, and then each electrode needle is slid into its pre-designated position by pushing each holder down its respective ramp. The leads of the various electrodes can then be connected to the measuring and monitoring equipment. This procedure can be easily done by those with minimal training in neuro-physiological measurements such as emergency personnel in a moving emergency vehicle on the way from an accident scene to a hospital so that data can be recorded for emergency room personnel by the time the emergency vehicle arrives.

A feature of the invention is the use of a holder with a stored position and an insertion-ready position. The stored position reduces the likelihood that the needles will not easily injure emergency personnel or become contaminated.

Another feature of the present invention is the combination of a slot in a ramp carried by the holder. This combination assures a controlled insertion. The insertion is precise in location and depth as well as the extent of penetration, i.e., the length of the electrode needle that is in the scalp when the needle is fully inserted, which helps to hold the electrode in place. The needle is also inserted in a straight line so that it does not stress the skin during or after insertion.

Features of the present electrode contribute to safety. These include the ability to lock the needle in a safe, stored configuration where it cannot easily be deployed by accident and thus makes needle stick and needle contamination unlikely; and the tabs on the ends can be hold points for the fingers of the user when inserting the needle to assure that accurate placement is maintained during insertion.

These and other features and their advantages will be readily apparent to those skilled in the art of neurophysiological measurement electrode design from a careful reading of the Detailed Description of Preferred Embodiments, accompanied by the following drawings.

BRIEF DESCRIPTION OF THE DRAWINGS

In the figures,

FIGS. 2A and 2B are side views of the electrode shown in FIG. 1 with ramp in the insertion-ready position in FIG. 2A and in the stored position in FIG. 3, according to an embodiment of the present invention; and FIG. 3 is a top view of the electrode shown in FIGS. 1 and 2.

DETAILED DESCRIPTION OF PREFERRED EMBODIMENTS

Figure 1:
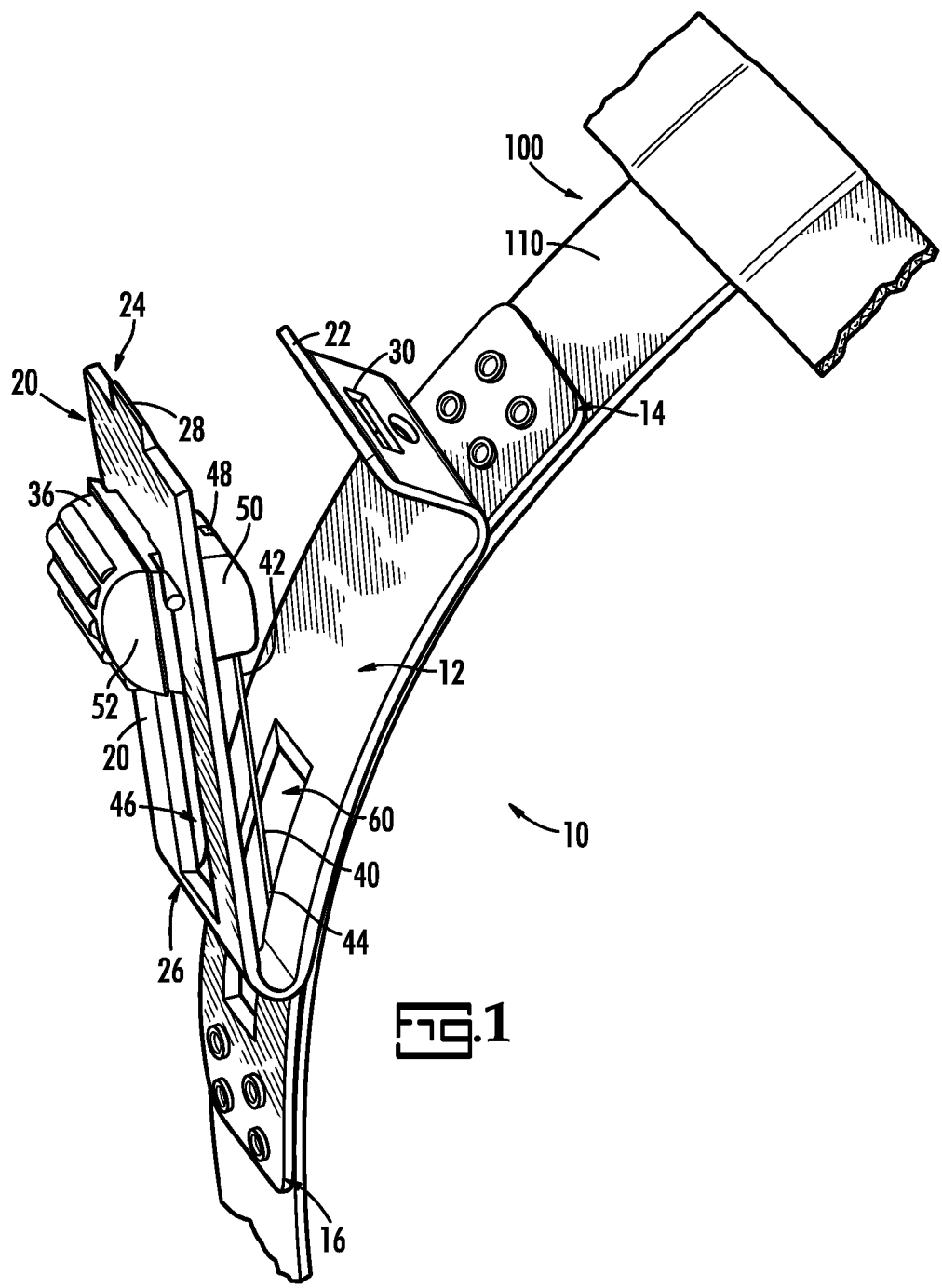
FIG. 1 is a perspective view of an electrode in use with a template cap, according to an embodiment of the present invention.

The present invention is an electrode for neurophysiological measurements and a template cap with an electrode for neurophysiological measurements. It is designed to simplify and accelerate the insertion of electrode needles in to the scalp of the patient when the patient is wearing the cap. Template caps are well known. See for example the template cap of Jordan, U.S. Pat. No. 6,510,340 and the net of Alkire, WO2008/119031, both of which are incorporated herein by reference.

Referring now to the FIGS. 1-3, there is shown the present electrode, generally indicated by reference number 10 on a template cap 100 attached to a strap 110 of template cap 100. Electrode 10 includes a base 12 that is preferably curved and may have holes formed in its proximal end 14 and its distal end 16 for sewing base 12 to strap 110 of template cap 100. Proximal end 14 and distal end 16 also serve as platforms for the thumb and forefinger of the user to steady electrode 10 prior to insertion of the electrode needle. Other forms of attachment that are convenient may be substituted for sewing base 12 to a cap. The orientation of electrode 10 and its components such as base 12 will be the same. Specifically, proximal will refer to the right end of electrode 10 as shown in FIG. 2 and distal will refer to the left end of electrode 10 in FIG. 2.

Electrode 10 has a resilient ramp 20 and a clip 22. Ramp has a proximal end 24 and a distal end 26. Proximal end 24 is nominally elevated from base 12 while distal end 26 is attached to base 12 near the distal end 16 of base 12. The proximal end 24 of ramp 20 may be formed with a tab 28 that fits into a slot 30 on clip 22 in a stored position when proximal end 24 of ramp 20 is pressed a sufficient distance toward base 12. Clip 22 is also resilient and, when pulled toward proximal end 14 of base 12, releases tab 28 from slot 30 so that proximal end 24 of ramp 20 springs up and away from proximal end 14 of base 12 to an insertion-ready position. Ramp 20 and clip 22 are preferably integrally formed with base 12 and made of a type and grade of plastic suitable for medical applications; that is, a type of plastic that is non-toxic and can be made and kept sterile prior to use.

The integral formation of ramp 20 and clip 22 defines a hinge that, when made of a resilient plastic, is sometimes called a living hinge. The user can adjust the angle of ramp 20 when about to insert the needle angle for entry as necessary.

Ramp 20 carries a holder 36 that in turn carries an electrode needle 40 oriented so that the long dimension of electrode needle 40 is parallel with the long dimension of ramp 20; that is, parallel to a line from proximal end 24 to a distal end 26 of ramp 20. Needle 40 may be centered over base 12 and has a proximal end 42 and a distal end 44; distal end 44 may be sharp. Needle 40 may be longer or shorter, or may vary in length from one position of a given template to another position on template cap 100.

When tab 28 of ramp 20 is inserted into slot 30 of clip 22, electrode 10 is then in the stored position. In this position, needle 40 cannot be inserted and distal end 44 of needle 40 is guarded by the plastic intersection of base 12 and ramp 20. Clip 22 has a low profile so it is less likely to catch on other equipment. When clip 22 is pulled toward proximal end 14 of base 12, tab 28 of ramp will be leased from slot 30 allowing proximal end 24 of ramp 20 to spring away from base 12. Electrode 10 is then in the insertion-ready position.

Holder 36 is carried by ramp 20 within a slot 46 formed in ramp 20. Slot 46 runs parallel to the long dimension of ramp 20 and is limited in its length to the distance distal end 44 of needle 40 is to be inserted into the scalp of the patient. Holder 36 includes a needle housing portion 50 below ramp 20 on one side of slot 46 and a thumb slide portion 52 above ramp 20 on the opposing side of slot 46. Housing portion 50 and thumb slide portion 52 may be integrally formed or snap-fitted together. A lead to neuro-physiological measuring and monitoring equipment can be connected to needle 40 via housing portion 50 through hole 48. Pressing on thumb slide portion 52 to drive it from proximal end 24 of ramp 20 toward distal end 26 of ramp, carries needle 40 forward toward distal end 16 of base 12 to the inserted position with needle 40 inserted in the scalp of the patient.

Base 12 has a small slot 60 formed therein and located so that needle 40, when electrode 10 is in the insertion-ready position, can be slid forward toward distal end 26 of ramp 20 where distal end 44 of needle will pass through slot 60 into the scalp of the user when electrode 10 is affixed to template cap 100. Needle 40 will enter scalp at a shallow angle suitable for both interacting electrically with the relevant portion of the patient's brain and remaining in place during the measurement. That angle of entry may be adjusted easily at the moment of use by the user by raising or lowering the needle slightly.

Those familiar with the design of electrodes for neurophysiological measurements will appreciate that many modifications and substitutions can be made to the foregoing preferred embodiments of the present invention without departing from the spirit and scope of the present invention, defined by the appended claims.

What is claimed is:

1. An electrode for neurophysiological measurements and for use with a template cap, said electrode comprising:
   (a) a base having a proximal end and a distal end, said base having a slot formed therein;
   (b) a ramp having a proximal end and a distal end, said distal end of said ramp being attached near said distal end of said base, said ramp having a slot running between said proximal end of said ramp and said distal end of said ramp;
   (c) a holder carried by said ramp in said slot of said ramp, said holder having a needle housing portion and a thumb drive portion; and
   (d) a needle having a proximal end and a distal end, said proximal end carried by said needle housing portion and said needle can be moved by pressing on said thumb drive portion and pushing said thumb drive portion from said proximal end to said distal end of said slot of said ramp thereby causing said distal end of said needle to pass from said base through said slot in said base.

2. The electrode of claim 1, said distal end of said ramp carrying a tab, and wherein said electrode further comprises a clip carried by said proximal end of said base, said clip having a slot dimensioned to receive said tab, wherein, when said tab is in said slot, said electrode is in a stored position, and wherein, when said tab is not in said slot of said clip and said needle is at said proximal end of said slot of said ramp, said electrode is in an insertion-ready position, and wherein, when said tab is not in said slot of said clip and said needle is at said distal end of said slot of said ramp, said electrode is in a needle-inserted position.

3. The electrode of claim 2, wherein said needle cannot be moved to said needle inserted position when said tab is in said slot of said clip.

4. The electrode of claim 1, wherein said slot of said ramp is dimensioned to limit insertion of said needle through said slot of said base.

5. The electrode of claim 1, wherein said ramp and said base are made to be at an angle, said angle being pre-determined to be the angle of insertion for said needle.

6. The electrode of claim 1, wherein said slot of said ramp has a long dimension running from said proximal end of said slot to said distal end of said slot, and wherein said holder holds said needle parallel to said long dimension.

7. The electrode of claim 1, wherein said holder holds said needle between said ramp and said base.

8. The electrode of claim 1, wherein said holder has said needle housing portion on one side of said slot of said ramp and said thumb drive portion on the other side of said slot of said ramp.

9. The electrode of claim 1, wherein said base is curved.

10. The electrode of claim 1, wherein said proximal and distal ends of said base have holes formed therein for securing said base to straps of a template cap.

11. A template cap with electrodes for neurophysiological measurements, said template cap comprising:

(a) straps secured together to form a cap for use on the head of a patient to undergo neurophysiological measurements; and
(b) plural electrodes prepositioned and secured to said straps, each electrode of said plural electrodes having
  (i) a base having a proximal end and a distal end, said base having a slot formed therein;
  (ii) a ramp having a proximal end and a distal end, said distal end of said ramp being attached near said distal end of said base, said ramp having a slot running between said proximal end of said ramp and said distal end of said ramp;
  (iii) a holder carried by said ramp in said slot of said ramp, said holder having a needle housing portion and a thumb drive portion; and
  (iv) a needle having a proximal end and a distal end, said proximal end carried by said needle housing portion and said needle oriented parallel to said slot so that said needle can be moved by pressing on said thumb drive portion and pushing said thumb drive portion from said proximal end to said distal end of said slot of said ramp thereby causing said distal end of said needle to pass through said slot in said base.

12. The template cap of claim 11, wherein said distal end of said ramp of said each electrode carries a tab, and wherein said each electrode further comprises a clip carried by said proximal end of said base, said clip having a slot dimensioned to receive said tab, wherein, when said tab is in said slot, said each electrode is in a stored position, and wherein, when said tab is not in said slot of said clip and said needle is at said proximal end of said slot of said ramp, said each electrode is in an insertion-ready position, and wherein, when said tab is not in said slot of said clip and said needle is at said distal end of said slot of said ramp, said each electrode is in a needle-inserted position.

13. The template cap of claim 12, wherein said needle of said each electrode cannot be moved to said needle inserted position when said tab is in said slot of said clip.

14. The template cap of claim 11, wherein said slot of said ramp of said each electrode is dimensioned to limit insertion of said needle through said slot of said base.

15. The template cap of claim 11, wherein said ramp and said base of said each electrode are made to be at an angle, said angle being pre-determined to be the angle of insertion for said needle.

16. The template cap of claim 11, wherein said slot of said ramp of said each electrode has a long dimension running from said proximal end of said slot to said distal end of said slot, and wherein said holder holds said needle parallel to said long dimension.

17. The template of claim 11, wherein said holder of said each electrode holds said needle between said ramp and said base.

18. The template cap of claim 11, wherein said holder of said each electrode has said needle housing portion on one side of said slot of said ramp and said thumb drive portion on the other side of said slot of said ramp.

19. The template cap of claim 11, wherein said base of said each electrode is curved.

20. The template cap of claim 11, wherein said proximal and distal ends of said base of said each electrode have holes formed therein for securing said base to said straps of said template cap.

* * * * *